United States Patent [19]

Bergander

[11] Patent Number: 4,789,827
[45] Date of Patent: Dec. 6, 1988

[54] MAGNETIC FLUX LEAKAGE PROBE WITH RADIALLY OFFSET COILS FOR USE IN NONDESTRUCTIVE TESTING OF PIPES AND TUBES

[75] Inventor: Mark J. Bergander, Madison, Conn.

[73] Assignee: Electric Power Research Institute, Palo Alto, Calif.

[21] Appl. No.: 927,616

[22] Filed: Oct. 31, 1986

[51] Int. Cl.⁴ .............................................. G01N 27/87
[52] U.S. Cl. ...................................... 324/220; 324/228; 324/242
[58] Field of Search ................. 324/219–221, 324/242–243, 228

[56] References Cited

U.S. PATENT DOCUMENTS

| 2,992,390 | 7/1961 | De Witte | 324/220 |
|---|---|---|---|
| 3,060,377 | 10/1962 | Schmidt | 324/220 |
| 3,284,701 | 11/1966 | Kerbow | 324/221 X |
| 3,443,211 | 5/1969 | Wood et al. | |
| 3,449,662 | 6/1969 | Wood | 324/220 |
| 3,532,969 | 10/1970 | McCullough et al. | |
| 3,535,624 | 10/1970 | Wood | |
| 3,597,678 | 8/1971 | Fearon | 324/220 |
| 3,899,734 | 8/1975 | Beaver et al. | 324/220 |
| 3,906,358 | 9/1975 | Stone | |
| 3,940,689 | 2/1976 | Johnson | 324/221 |
| 3,949,292 | 4/1976 | Beaver et al. | |
| 3,967,194 | 6/1976 | Beaver et al. | |
| 4,088,946 | 5/1978 | Charles et al. | 324/220 |
| 4,188,577 | 2/1980 | Mhatre et al. | 324/232 X |
| 4,330,748 | 5/1982 | Holden | 324/220 X |
| 4,447,777 | 5/1984 | Sharp et al. | 324/220 |
| 4,468,619 | 8/1984 | Reeves | 324/220 |

FOREIGN PATENT DOCUMENTS

| 0101044 | 8/1980 | Japan | 324/220 |
|---|---|---|---|
| 0217160 | 12/1984 | Japan | 324/220 |
| 0051779 | 9/1966 | Poland | 324/220 |
| 1032343 | 6/1966 | United Kingdom | 324/228 |
| 1567166 | 5/1980 | United Kingdom | 324/220 |

*Primary Examiner*—Gerard R. Strecker
*Attorney, Agent, or Firm*—Flehr, Hohbach, Test, Albritton & Herbert

[57] ABSTRACT

A magnetic flux detection probe for use in nondestructive testing of tubular products includes first and second flux leakage sensing coils mounted within a probe housing and radially offset with respect to each other to provide improved detection of defect locations and magnitudes. In a preferred embodiment a Hall effect sensing device is provided in the probe to sense variations in wall thickness of a tubular product while the flux leakage coils identify sharp responses of cracks and pits in the wall structure.

3 Claims, 3 Drawing Sheets

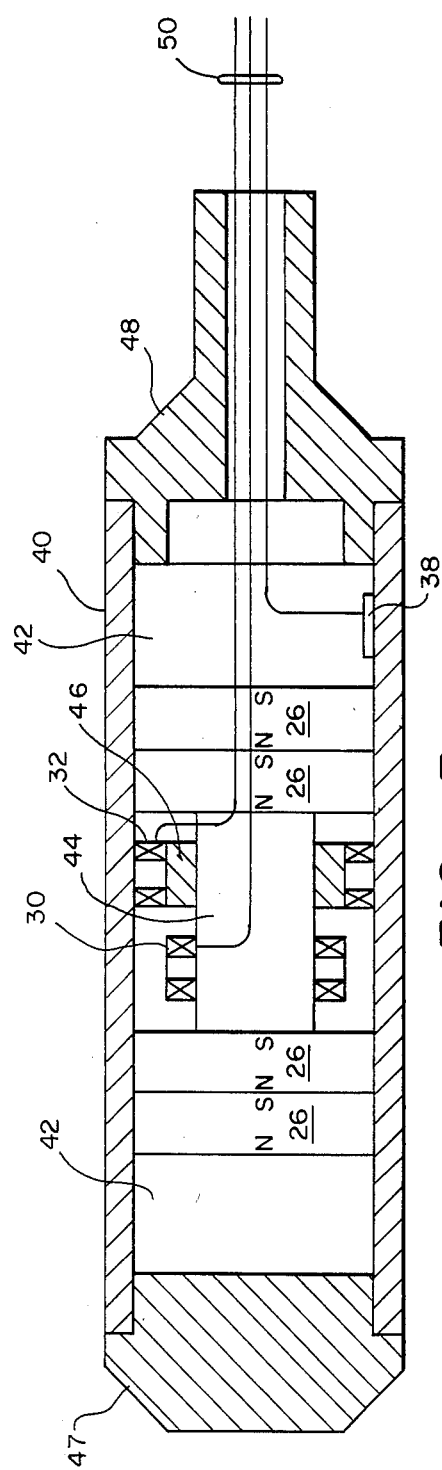
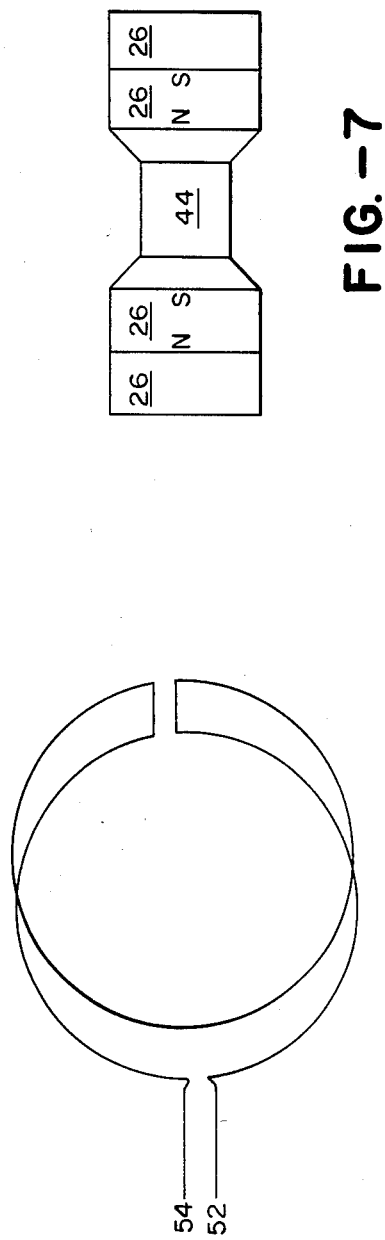
FIG.-3
FIG.-7
FIG.-4

| LOCATION: | A | B | C | D | E | F | G | H |
|---|---|---|---|---|---|---|---|---|
| DIA/WIDTH: | 1/16 | 1/8 | .067 | 5/64 | 7/64 | 3/16 | 3/16 | 1/8 |
| DEPTH: | .017 | THRU 62 | THRU | .066 | .050 | .033 | .017 | .099 |
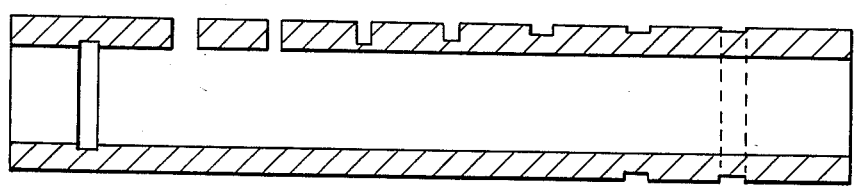
FIG.—5A
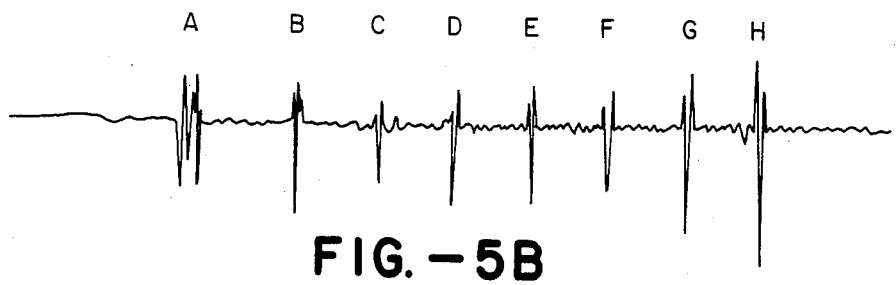
FIG.—5B
| LOCATION: | A | B | C | D | E |
|---|---|---|---|---|---|
| DEPTH: | .017 | .025 | .033 | .047 | .050 |
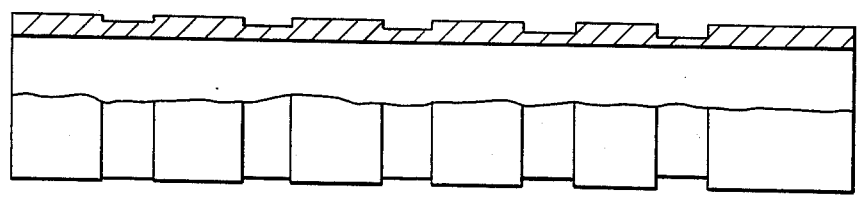
FIG.—6A
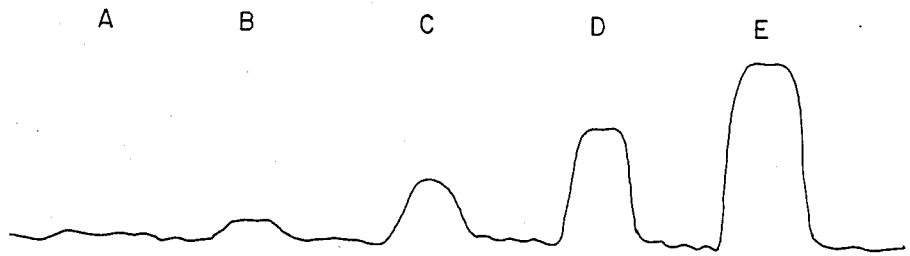
FIG.—6B

MAGNETIC FLUX LEAKAGE PROBE WITH RADIALLY OFFSET COILS FOR USE IN NONDESTRUCTIVE TESTING OF PIPES AND TUBES

BACKGROUND OF THE INVENTION

This invention relates generally to nondestructive testing of pipe and tubing using magnetic flux leakage inspection, and more particularly the invention relates to a probe for use in such testing.

The use of magnetic flux leakage inspection of pipes and tubing is well known in the art of nondestructive testing. A magnetic field is established in the material undergoing inspection, and a sensor detects changes in flux patterns at the surface of the material due to cracks, pits, or wall thickness variations. Heretofore, eddy current coil detectors have been employed to detect sharp responses due to defects such as cracks and pits, while Hall effect sensors have been employed to detect more gradual responses due to wall thinning, for example.

In recent years, special ferritic alloys and carbon steel tubes have been employed in heat-exchanger tubing. These materials present a problem for in-service inspection due to their highly ferromagnetic properties. These properties severely limit the application of standard eddy current techniques which are widely used for non-magnetic tubing inspection. Presently, eddy current sensors with magnetic saturation are used on a limited basis for ferrous tube inspection. However, this method has several disadvantages including detecting false indications due to permeability variations, insensitivity to gradual types of tube defects, need for tube cooling during inspection, and complicated and expensive probes and instrumentation. Thus, there is a recognized, industry-wide need for a better method and apparatus for nondestructive ferrous tube inspection.

SUMMARY OF THE INVENTION

An object of the invention is an improved probe for use in nondestructive testing of ferritic stainless steel and carbon steel tubing.

Another object of the invention is a magnetic flus leakage probe which is responsive to both sharp and gradual magnetic flux changes due to material defects.

Still another object of the invention is a probe that is readily manufactured and used for nondestructive insevice inspection of pipe and tubing.

A feature of the invention is the use of a plurality of flux leakage coil sensors positioned in a probe for different spacing from a surface undergoing inspection.

Another feature of the invention is the use of flux leakage coils which are configured to respond to radial components of flux leakage at the inner surfaces of tubes and pipes.

Still another feature of the invention is the provision of a Hall-effect sensor along with flux leakage coil sensors to facilitate the detection of gradual changes due to wall thickness variations, for example.

Briefly, a probe in accordance with the invention includes a generally cylindrical housing in which is mounted magnetic means for establishing a flux pattern in the body of a tube or pipe undergoing inspection. A plurality of coils is mounted in the housing at different radii whereby the coils are spaced differently from the inner surface of the material undergoing inspection.

Comparison of signals from the two coils facilitates identification of the damage point and the approximate severity of the damage. Each coil is designed to provide a response to the perpendicular or radial component of flux leakage produced around a defect.

In a preferred embodiment, a Hall-effect sensor is provided in the probe and spaced from the flux leakage sensing coils for detecting flux changes due to wall thickness variations. Thus, sharp response effects such as pits and cracks are readily discernible along with wall thinning defects.

The invention and objects and features thereof will be more readily apparent from the following detailed description and appended claims when taken with the drawing.

BRIEF DESCRIPTION OF THE DRAWING

FIG. 3 is a section view of a probe in accordance with one embodiment of the invention.

FIG. 4 is a section view of one turn of a coil in the probe in accordance with the preferred embodiment.

FIGS. 5A and 5B are a section view of a tube illustrating defects therein and signals generated by the probe in accordance with the invention in response to the defects, respectively.

FIGS. 6A and 6B are a partial section view of a tube having defects and a signal generated by the probe in accordance with the invention in response to the defects, respectively.

FIG. 7 is a plan view of magnetic source means for use in the probe in accordance with an alternative embodiment.

DETAILED DESCRIPTION OF ILLUSTRATIVE EMBODIMENT

Figure 1:
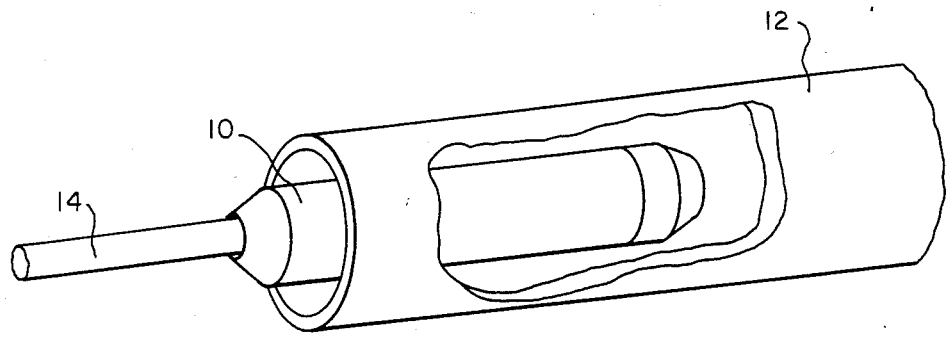
FIG. 1 is a persective view of a probe in accordance with the invention shown in its operating environment.

FIG. 1 is a perspective view of a probe 10 in accordance with the invention positioned in its operating environment within a tube 12 which is shown partially in section to further illustrate the positioning of probe 10 therein. The probe 10 is pulled through the tube by means of a cord 14 in which electrical connections to the probe sensing elements are provided.

Figure 2:
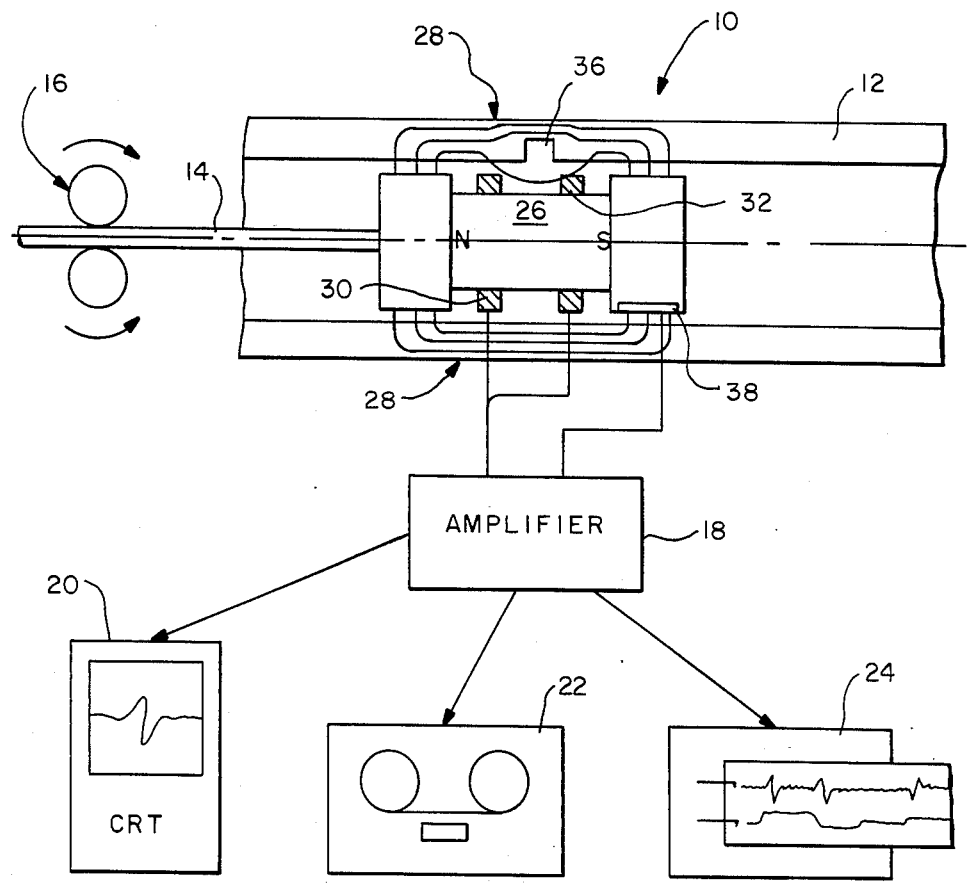
FIG. 2 is a functional block diagram of a magnetic flux leakage test sysem employing a probe in accordance with the invention shown in section view.

FIG. 2 is a functional block diagram of the nondestructive testing system including the probe 10 which is shown schematically in section view within the tube 12. The cord 14 is pulled by means of pusher-puller rollers 16, and electrical signals from the probe sensing elements are connected through an amplifier 18 to suitable recording means such as a CRT 20, a magnetic tape 22, or a strip chart recorder 24.

Looking particularly at the schematic diagram of the probe 10, magnetic means 26 establishes flux patterns, shown generally at 28, that pass through the wall of tube 12 in a closed magnetic loop. In accordance with the invention, a plurality of coils 30 and 32 is provided in the probe structure to monitor flux leakage such as the flux pattern at the pit 36 in the internal surface of tube 12. In a preferred embodiment of the invention, a Hall sensor 38 is provided for monitoring the flux pattern also.

Consider now the section view of the probe illustrated in FIG. 3 which more particularly illustrates a preferred embodiment of the probe. The probe comprises a housing 40 in which are positioned four permanent magnets 26 and a magnetic connector 44 which, together with magnet pole pieces 42, provide an internal magnetic flux path within the probe. When the probe is positioned within a tube or pipe for inspection, the flux leaves one pole piece, travels through the wall of the pipe, and re-enters the probe at the other pole piece.

Mounted directly to the outer surface of connector 44 is the first coil 30, while the second coil 32 is mounted on the connector 44 by means of a spacer 46 whereby the two coils 30, 32 are radially displaced. The radial displacement of the two coils has proved to be advantageous in identifying both the location of defects and the magnitude of the defects.

The Hall-effect sensor 38 is mounted between one pole piece 42 and the housing 40 of the probe for sensing flux lines between the pole piece and the tube undergoing inspection. One end of the probe is sealed by a plug 47 while the other end of the probe receives a plug 48 having an internal opening through which the electrical connectors 50 to the Hall-effect device and coils pass. Cord 14 (not shown) extends outwardly from the plug 48.

In accordance with one feature of the invention, the turns of the two coils 30 and 32 are configured to sense radially oriented flux. This is illustrated in one turn of a coil in the perspective view of FIG. 4. Leads 52, 54 are interconnected to the turn, and it will be noted that the turn is annularly shaped for positioning on the connector 44 or the spacer 46 affixed to the cylindrical connector 44.

The use of the two radially displaced coils has proved to be particularly advantageous in identifying the location and magnitude of defects such as pits and cracks. This is illustrated in FIGS. 5A and 5B, where FIG. 5A shows a section view of a length of test pipe 62 having defects A-H located therein. The diameter-to-width ratio of the defects, and the depths of the defects, are noted in FIG. 5A. FIG. 5B illustrates a strip chart printout of one of the signals generated by the two radially offset coils as the coils in the test probe are passed through the pipe in proximity to the defects. Each coil is separately connected with a channel of the electronic amplifier. It is seen that the coils provide a flux leakage signal response for the calibration tube having spikes positioned in time to correspond with the location of the defects and with the magnitudes of the signal spikes corresponding to the magnitudes of the defects. By comparison of signal amplitudes from both channels, defect depth and point of origin can be determined.

Similarly, variations in thickness of the tube wall are detected by the Hall-effect device as illustrated in FIGS. 6A and 6B which show a section view of a pipe having wall thickness variations at locations A-E as shown in FIG. 6A and the signal from the Hall-effect device shown in FIG. 6B. It is noted that the Hall-effect device generates a signal whenever the thickness of the calibration pipe varies, and the magnitude of the signal is directly proportional to the magnitude of the change in thickness.

The embodiment of the probe illustrated in FIG. 3 is particularly advantageous in inspecting pipes and tubing having relatively thin walls. For a thick-walled tube, the magnetic circuit illustrated in FIG. 7 is preferred. Like elements in FIGS. 3 and 7 have the same reference numerals. The primarily difference in the circuit is the bevelled or tapered end portions of the soft steel connector 44 to facilitate the transfer of flux between the magnets and the connector 44.

The magnetic flux leakage probe employing a plurality of radially offset flux leakage coils and preferably with a Hall-effect sensor has proved to be particularly useful in sensing defects in pipes and tubing of ferritic alloys and carbon steel material.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

I claim:

1. A magnetic flux detection probe for use in nondestructive testing of tubes and the like, comprising:
   a generally cylindrical housing having a central axis;
   magnetic means positioned within said housing for establishing a magnetic flux pattern passing through the wall of a tube undergoing test, said magnetic means including first and second pole pieces, first and second magnets between said first and second pole pieces, and a magnetic connector between said first and second magnets, all axially aligned in said housing whereby magnetic flux from said first and second magnets leaves said first pole piece, travels through a tube undergoing test and re-enters the housing through said second pole piece;
   a first coil positioned on and around said connector within said housing and a second coil positioned on a spacer on said connector and around said connector and radially offset within said housing from said first coil, said first and second coils generating two signals for use in detecting the location and magnitude of defects by detecting magnetic leakage flux from a tube undergoing test due to cracks and pits;
   electrical conductor means connected to said first coil and said second coil and extending from said probe for transmitting separate electrical signals from said first coil and said second coil;
   a Hall effect sensing device positioned within said housing for sensing changes in magnetic flux patterns in a tube undergoing test and thereby sensing variations in tube wall thickness; and
   electrical conductor means connected to said Hall effect sensing device and extending from said probe for transmitting electrical signals from said Hall effect sensing device.

2. The probe as defined by claim 1 wherein each coil comprises a plurality of turns of wire with each turn configured to sense a component of magnetic flux leakage perpendicular to the inner surface of a tube undergoing test.

3. The probe as defined by claim 1 wherein said Hall effect sensing device is mounted to one of said pole pieces abutting said housing.

* * * * *